(12) United States Patent
Neubardt et al.

(10) Patent No.: US 8,326,414 B2
(45) Date of Patent: Dec. 4, 2012

(54) NERVE STIMULATING DRILL BIT

(75) Inventors: Seth L. Neubardt, Mamaroneck, NY (US); William Keith Adcox, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1352 days.

(21) Appl. No.: 11/738,113

(22) Filed: Apr. 20, 2007

(65) Prior Publication Data

US 2008/0262526 A1  Oct. 23, 2008

(51) Int. Cl.
*A61N 1/00* (2006.01)
(52) U.S. Cl. ............. 607/2; 607/116; 607/118; 607/127
(58) Field of Classification Search .............. 607/2, 116, 607/118, 127
See application file for complete search history.

(56) References Cited

U.S. PATENT DOCUMENTS

| | | | | |
|---|---|---|---|---|
| 4,627,439 A * | 12/1986 | Harris | .................. | 166/272.5 |
| 4,630,611 A * | 12/1986 | King | .................. | 600/377 |
| 5,196,015 A | 3/1993 | Neubardt | | |
| 5,456,707 A * | 10/1995 | Giele | .................. | 607/127 |
| 5,474,558 A | 12/1995 | Neubardt | | |
| 6,796,985 B2 | 9/2004 | Bolger et al. | | |
| 7,079,883 B2 | 7/2006 | Marino et al. | | |
| 7,177,677 B2 | 2/2007 | Kaula et al. | | |
| 2004/0243207 A1* | 12/2004 | Olson et al. | .................. | 607/116 |
| 2005/0004623 A1 | 1/2005 | Miles et al. | | |
| 2006/0173374 A1 | 8/2006 | Neubardt et al. | | |
| 2006/0178593 A1 | 8/2006 | Neubardt et al. | | |
| 2006/0178594 A1 | 8/2006 | Neubardt et al. | | |
| 2006/0200023 A1 | 9/2006 | Melkent et al. | | |

* cited by examiner

*Primary Examiner* — Nicole F Lavert (57) ABSTRACT

A nerve stimulating drill bit is provided and can include a shank and a body attached to the shank. The body can include a plurality of flutes and a cutting tip. Further, a first conductor can extend through the shank and the body. The first conductor can be insulated and can provide a signal at the cutting tip. Further, the signal can be configured to provide nerve stimulation at the cutting tip of the nerve stimulating drill bit.

25 Claims, 11 Drawing Sheets

NERVE STIMULATING DRILL BIT

FIELD OF THE DISCLOSURE

The present disclosure relates generally to spinal fixation devices. More specifically, the present disclosure relates to devices for stimulating nerves while drilling pilot holes for bone screws.

BACKGROUND

Certain spinal deformities, e.g., scoliosis, can be treated using a spinal fixation system. The spinal fixation system is a brace that can be installed along a spinal column in order to prevent further bending of the spine and to coax the spine into a relatively straighter position. The spinal fixation system can include a plurality of anchorage components. Further, one or more longitudinal elements can be installed along the anchorage components. Each anchorage component can be affixed to a corresponding vertebra using one or more bone screws, e.g., pedicle screws. The pedicle screws can be installed in a pedicle wall of a vertebra. Further, the pedicle screws are relatively strong and can provide stability for each anchorage component and the spinal fixation system.

Bone screws can be used in other surgical applications. For example, fixation and motion preserving devices can be used in other orthopedic surgeries, e.g., knee surgeries, hip surgeries, etc. These fixation and motion preserving devices may require the use of one or more bone screws that may be placed in close proximity to neural structures in order to hold the device in place.

During the installation of a fixation or motion preserving device or system, it may be necessary to drill a pilot hole for one or more bone screws. Further, great care should be used to avoid nerve impingement when drilling the pilot holes. Otherwise, a patient may be injured during the installation and suffer a loss of mobility of another part of the body due to the nerve impingement.

Accordingly, there is a need for a device for stimulating nerves while drilling a pilot hole for a bone screw.

DETAILED DESCRIPTION OF THE DRAWINGS

A nerve stimulating drill bit is provided and can include a shank and a body attached to the shank. The body can include a plurality of flutes and a cutting tip. Further, a first conductor can extend through the shank and the body. The first conductor can be insulated and can provide a signal at the cutting tip. Further, the signal can be configured to provide nerve stimulation at the cutting tip of the nerve stimulating drill bit.

In another embodiment, a method of treating a patient is disclosed and can include energizing a nerve stimulating drill bit. When energized, the nerve stimulating drill bit can provide a nerve stimulation signal at a cutting tip of the nerve stimulating drill bit. The method can also include advancing the nerve stimulating drill bit into tissue in order to cut a hole in the tissue.

In yet another embodiment, a nerve stimulating drill bit is disclosed and can include a shank and a body. A first conductor can extend along the shank and body. Also, a second conductor can extend along the shank and body. The nerve stimulating drill bit can transmit a signal via the first conductor and receive at least a portion of the signal via the second conductor.

Description of a First Embodiment of a Nerve Stimulating Drill Bit

Figure 1:
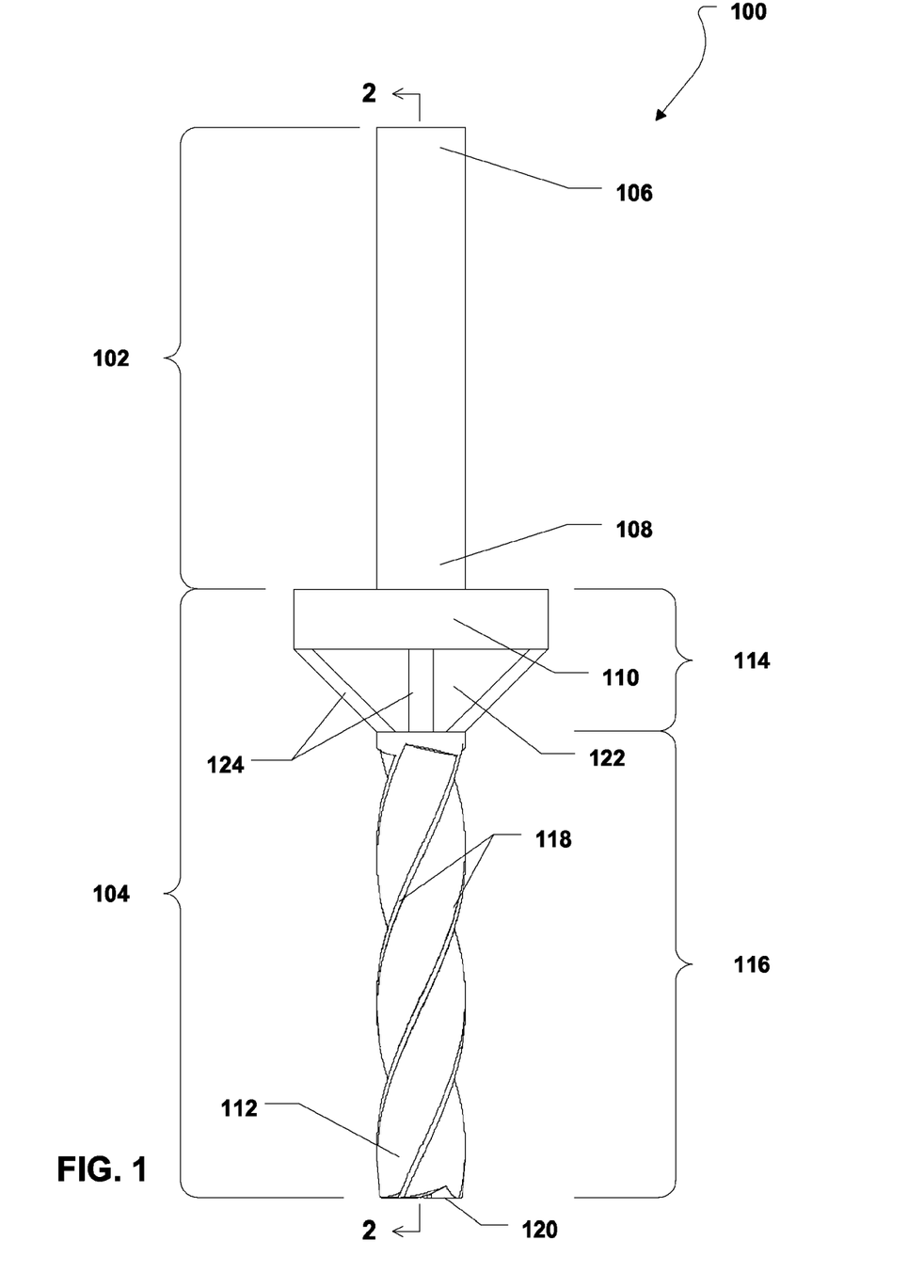
FIG. 1 is a plan view of a first embodiment of a nerve stimulating drill bit.
Figure 2:
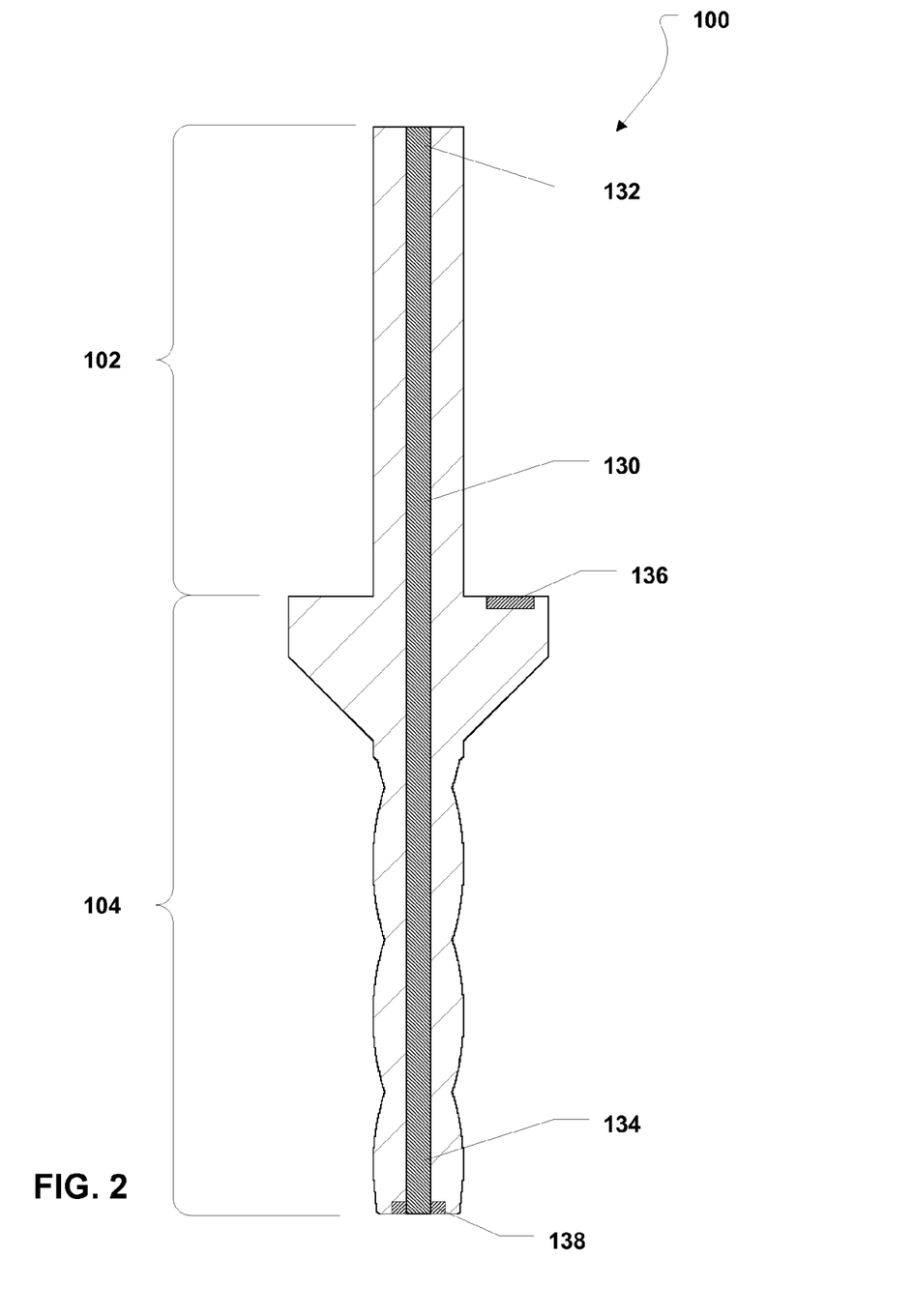
FIG. 2 is a cross-section view of the first embodiment of the nerve stimulating drill bit taken along line 2-2 in FIG. 1.

Referring to FIG. 1 and FIG. 2, a first embodiment of a nerve stimulating drill bit is shown and is generally designated 100. As shown in FIG. 1, the nerve stimulating drill bit 100 can include a shank 102 and a body 104 extending therefrom. The shank 102 can include a proximal end 106 and a distal end 108. Further, the body 104 can extend from the distal end 108 of the shank 102.

FIG. 1 illustrates that the body 104 can include a proximal end 110 and a distal end 112. Additionally, the body 104 can include a first portion 114 and a second portion 116. The first portion 114 of the body 104 can be generally frusto-conically shaped and can taper from the proximal end 110 of the body 104 toward the second portion 116 of the body 104. The second portion 116 can be generally cylindrical and can extend from the first portion 114 of the body 104 to the distal end 112 of the body 104.

As shown in FIG. 1, the second portion 116 of the body 104 can include a plurality of flutes 118 that can extend helically along the length of the second portion 116 of the body 104 from the interface with the first portion 114 of the body 104 to a cutting tip 120 at the distal end 112 of the body 104. FIG. 1 shows that the first portion 114 of the body 104 can include an angled outer perimeter 122. Moreover, a plurality of angled cutting edges 124 can extend along the angled outer perimeter 122 of the first portion 114 of the body 104.

During use, the second portion 116 of the body 104 can be used to cut a cylindrical hole in tissue, e.g., bone, and the first portion 114 of the body 104 can be used to cut an angled hole at the opening of the hole cut by the second portion 116. Accordingly, the angled portion of the hole cut using the nerve stimulating drill bit 100 can be considered a countersink portion and can allow a bone screw installed in the hole to be counter sunk in the tissue.

In a particular embodiment, the shank 102 can be generally cylindrical and can be sized and shaped to be received within a drill chuck, e.g., a keyed drill chuck, a keyless drill chuck, or any other type of drill chuck well known in the art. Alternatively, the shank 102 can be formed with a plurality of flat surfaces that will allow the drill chuck to grip the shank 102 and prevent the nerve stimulating drill bit 100 from moving within the drill chuck after the drill chuck is tightened there around.

In a particular embodiment, the shank 102 and the body 104 of the nerve stimulating drill bit 100 can be made from a dielectric material, i.e., a material that cannot conduct electricity. For example, the dielectric material can be a polymer material, a ceramic material, or a combination thereof. The polymer materials can include polyaramide materials, polyimid materials, polyamide materials, polyaryletherketone (PAEK) materials, or a combination thereof. The PAEK materials can include polyetherketone (PEK), polyetheretherketone (PEEK), polyetherketoneketone (PEKK), polyetherketoneetherketoneketone (PEKEKK), or a combination thereof. The ceramic materials can include alumina oxide, silica oxide, zirconium oxide, aluminum oxide, or a combination thereof.

Referring to FIG. 2, a cross-section of the nerve stimulating drill bit 100 is shown. As illustrated in FIG. 2, the nerve stimulating drill bit 100 can include a generally cylindrical conductor 130 therein. In a particular embodiment, the conductor 130 can include a proximal end 132 and a distal end 134. Further, the conductor 130 can be made from a conductive material, e.g., a metal material. The metal material can be a pure metal, a metal alloy, or a combination thereof. The pure metal can include aluminum, copper, gold, titanium, or a combination thereof. The metal alloy can include stainless steel, tungsten carbide, a cobalt-chrome-molybdenum alloy, a titanium alloy, or a combination thereof.

When the nerve stimulating drill bit 100 is installed in a surgical drill, the proximal end 132 of the conductor 130 can engage a power source that can be used to provide an electric signal to the conductor 130. The electric signal can have a constant current that is less than or equal to fifty milliamps (50 ma). Since the shank 102 and the body 104 of the nerve stimulating drill bit 100 are made from a dielectric material, only the conductor 130 can conduct electricity through the nerve stimulating drill bit 100. As such, the nerve stimulating drill bit 100 is configured so the distal end 134 of the conductor 130 can stimulate tissue proximate to the cutting tip 120 of the nerve stimulating drill bit 100. The body 104 of the nerve stimulating drill bit 100 can substantially insulate other tissue surrounding the nerve stimulating drill bit 100 from the signal provided to the conductor 130.

In an alternative embodiment, the nerve stimulating drill bit 100 can be rotated manually, e.g., by a manually operated drill or by a handle affixed directly to the nerve stimulating drill bit 100.

FIG. 2 also illustrates that the nerve stimulating drill bit 100 can include a radio frequency identification (RFID) device 136 incorporated therein. For example, the RFID device 136 can be incorporated into the body 104 of the nerve stimulating drill bit 100. Further, the RFID device 136 can be passive and can be powered by an RFID reader placed near the nerve stimulating drill bit 100. Alternatively, the RFID device 136 can be active and the nerve stimulating drill bit 100 can include a power source, such as a battery (not shown). In a particular embodiment, the RFID device 136 can identify a size of the nerve stimulating drill bit 100; a date of manufacture of the nerve stimulating drill bit 100; a lot code associated with the production of the nerve stimulating drill bit 100; a type of material, or materials, comprising the nerve stimulating drill bit 100; or a combination thereof.

As further shown in FIG. 2, the nerve stimulating drill bit 100 can include a guide device 138 incorporated into the distal end 112 of the body 104. The guide device 138 can be radiopaque and can aid in navigating the cutting tip 120 of the nerve stimulating drill bit 100 as the nerve stimulating drill bit 100 is advanced into tissue.

Description of a Second Embodiment of a Nerve Stimulating Drill Bit

Figure 3:
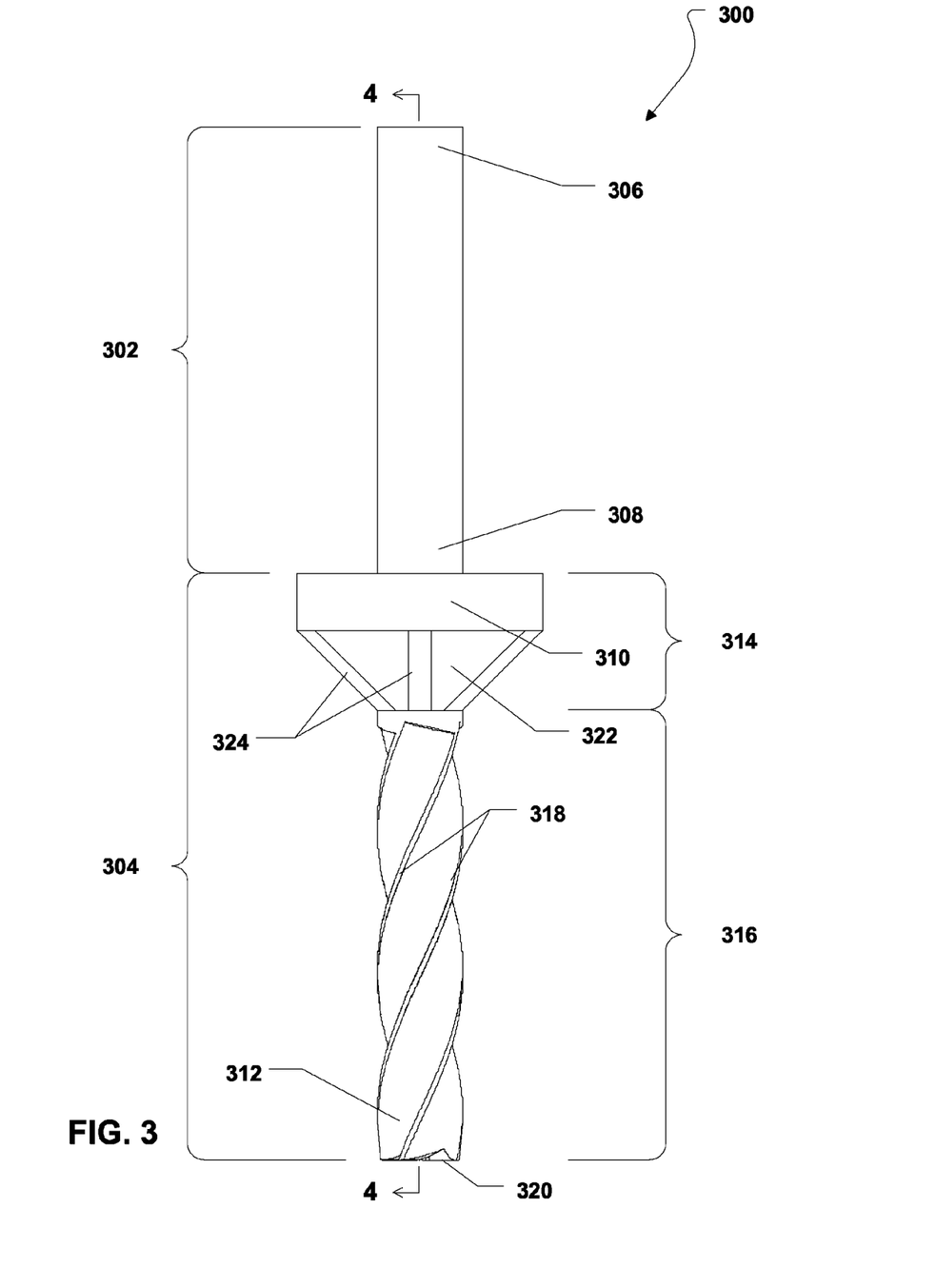
FIG. 3 is a plan view of a second embodiment of a nerve stimulating drill bit.
Figure 4:
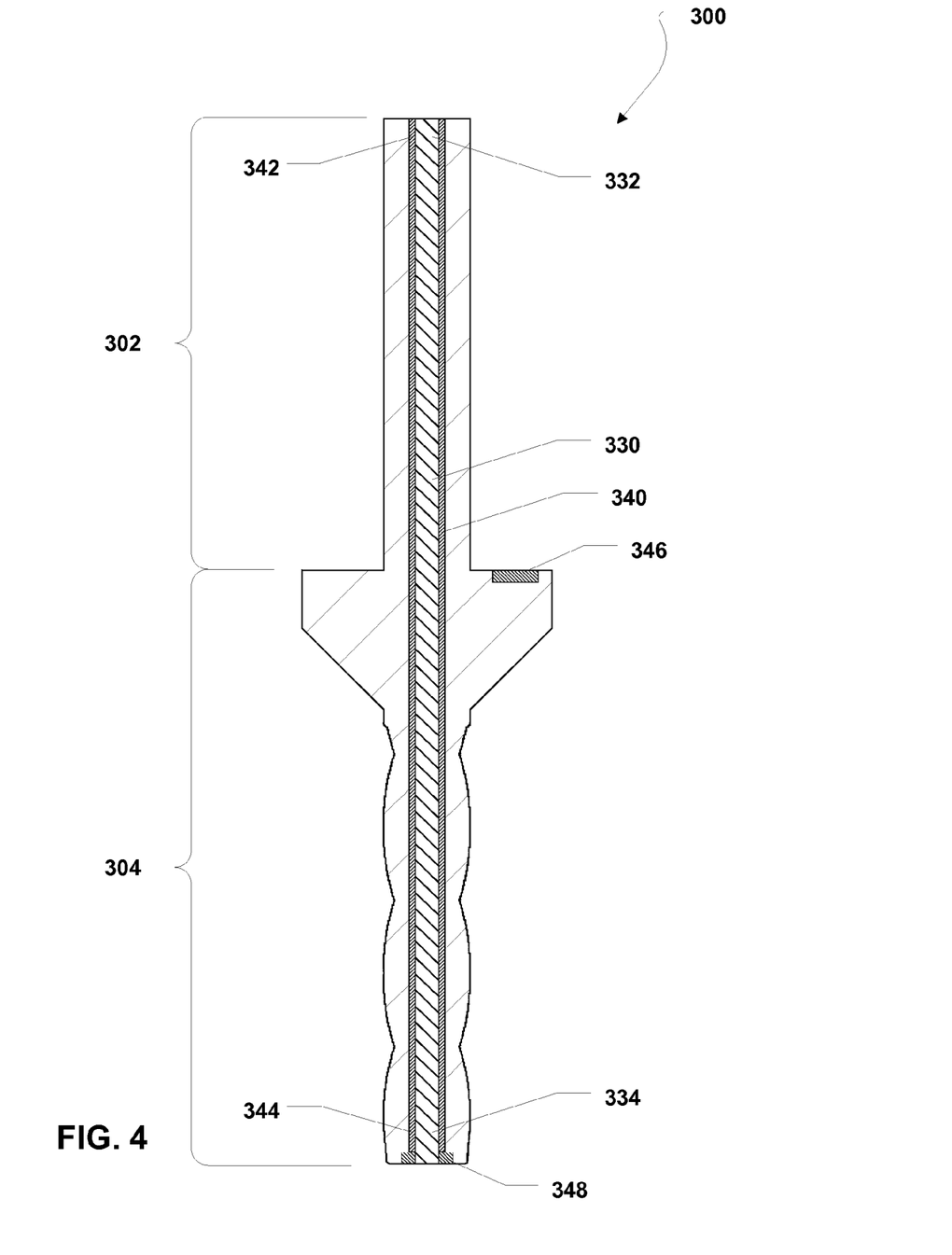
FIG. 4 is a cross-section view of the second embodiment of a nerve stimulating drill bit taken along line 4-4 in FIG. 3.

Referring to FIG. 3 and FIG. 4, a second embodiment of a nerve stimulating drill bit is shown and is generally designated 300. As shown in FIG. 3, the nerve stimulating drill bit 300 can include a shank 302 and a body 304 extending therefrom. The shank 302 can include a proximal end 306 and a distal end 308. Further, the body 304 can extend from the distal end 308 of the shank 302.

FIG. 3 illustrates that the body 304 can include a proximal end 310 and a distal end 312. Additionally, the body 304 can include a first portion 314 and a second portion 316. The first portion 314 of the body 304 can be generally frusto-conically shaped and can taper from the proximal end 310 of the body 304 toward the second portion 316 of the body 304. The second portion 316 can be generally cylindrical and can extend from the first portion 314 of the body 304 to the distal end 312 of the body 304.

As shown in FIG. 3, the second portion 316 of the body 304 can include a plurality of flutes 318 that can extend helically along the length of the second portion 316 of the body 304 from the interface with the first portion 314 of the body 304 to a cutting tip 320 at the distal end 312 of the body 304. FIG. 3 shows that the first portion 314 of the body 304 can include an angled outer perimeter 322. Moreover, a plurality of angled cutting edges 324 can extend along the angled outer perimeter 322 of the first portion 314 of the body 304.

During use, the second portion 316 of the body 304 can be used to cut a cylindrical hole in tissue, e.g., bone, and the first portion 314 of the body 304 can be used to cut an angled hole at the opening of the hole cut by the second portion 316. Accordingly, the angled portion of the hole cut using the nerve stimulating drill bit 300 can be considered a countersink portion and can allow a bone screw installed in the hole to be counter sunk in the tissue.

In a particular embodiment, the shank 302 can be generally cylindrical and can be sized and shaped to be received within a drill chuck, e.g., a keyed drill chuck, a keyless drill chuck, or any other type of drill chuck well known in the art. Alternatively, the shank 302 can be formed with a plurality of flat surfaces that will allow the drill chuck to grip the shank 302 and prevent the nerve stimulating drill bit 300 from moving within the drill chuck after the drill chuck is tightened there around.

In a particular embodiment, the shank 302 and the body 304 of the nerve stimulating drill bit 300 can be made from a metal material. The metal material can be a pure metal, a metal alloy, or a combination thereof. The pure metal can include titanium. The metal alloy can include stainless steel, tungsten carbide, a cobalt-chrome-molybdenum alloy, a titanium alloy, or a combination thereof.

Referring to FIG. 4, a cross-section of the nerve stimulating drill bit 300 is shown. As illustrated in FIG. 4, the nerve stimulating drill bit 300 can include a generally cylindrical conductor 330 therein. In a particular embodiment, the conductor 330 can include a proximal end 332 and a distal end 334. Further, the conductor 330 can be made from a conductive material, e.g., a metal material. The metal material can be a pure metal, a metal alloy, or a combination thereof. The pure metal can include aluminum, copper, gold, titanium, or a combination thereof. The metal alloy can include stainless steel, tungsten carbide, a cobalt-chrome-molybdenum alloy, a titanium alloy, or a combination thereof.

FIG. 4 shows that an insulator 340 can surround the conductor 330. The insulator 340 can be generally hollow and generally cylindrical. Further, the insulator 340 can have a proximal end 342 and a distal end 344. In a particular embodiment, the insulator 340 can be made from a dielectric material, i.e., a material that cannot conduct electricity. For example, the dielectric material can be a polymer material, a ceramic material, or a combination thereof. The polymer materials can include polyaramide materials, polyimid materials, polyamide materials, polyaryletherketone (PAEK) materials, or a combination thereof. The PAEK materials can include polyetherketone (PEK), polyetheretherketone (PEEK), polyetherketoneketone (PEKK), polyetherketoneetherketoneketone (PEKEKK), or a combination thereof. The ceramic materials can include alumina oxide, silica oxide, zirconium oxide, aluminum oxide, or a combination thereof.

When the nerve stimulating drill bit 300 is installed in a surgical drill, the proximal end 332 of the conductor 330 can engage a power source that can be used to provide an electric signal to the conductor 330. The electric signal can have a constant current that is less than or equal to fifty milliamps (50 ma). The insulator 340 can insulate the shank 302 and the body 304 of the nerve stimulating drill bit 300 from the electric signal traveling through the conductor 330 and only the conductor 330 can conduct electricity through the nerve stimulating drill bit 300. As such, the nerve stimulating drill bit 300 is configured so the distal end 334 of the conductor 330 can stimulate tissue proximate to the cutting tip 320 of the nerve stimulating drill bit 300. The insulator 340 within the nerve stimulating drill bit 300 can substantially insulate other tissue surrounding the nerve stimulating drill bit 300 from the signal provided to the conductor 330.

In an alternative embodiment, the nerve stimulating drill bit 300 can be rotated manually, e.g., by a manually operated drill or by a handle affixed directly to the nerve stimulating drill bit 300.

FIG. 4 also illustrates that the nerve stimulating drill bit 300 can include a radio frequency identification (RFID) device 346 incorporated therein. For example, the RFID device 346 can be incorporated into the body 304 of the nerve stimulating drill bit 300. Further, the RFID device 346 can be passive and can be powered by an RFID reader placed near the nerve stimulating drill bit 300. Alternatively, the RFID device 346 can be active and the nerve stimulating drill bit 300 can include a power source, such as a battery (not shown). In a particular embodiment, the RFID device 346 can identify a size of the nerve stimulating drill bit 300; a date of manufacture of the nerve stimulating drill bit 300; a lot code associated with the production of the nerve stimulating drill bit 300; a type of material, or materials, comprising the nerve stimulating drill bit 300; or a combination thereof.

As further shown in FIG. 4, the nerve stimulating drill bit 300 can include a guide device 348 incorporated into the distal end 312 of the body 304. The guide device 348 can be radiopaque and can aid in navigating the cutting tip 320 of the nerve stimulating drill bit 300 as the nerve stimulating drill bit 300 is advanced into tissue.

Description of a Third Embodiment of a Nerve Stimulating Drill Bit

Figure 5:
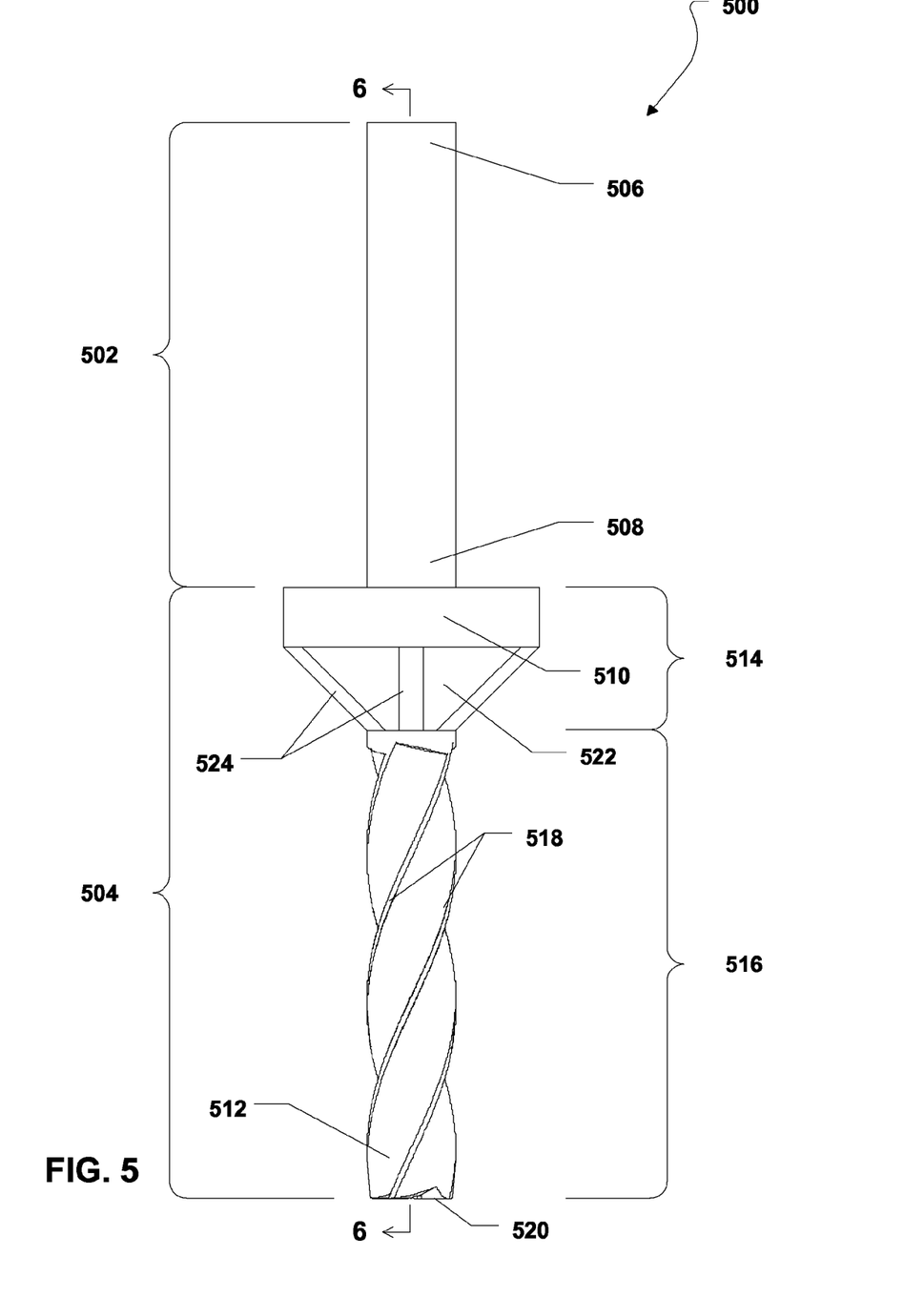
FIG. 5 is a plan view of a third embodiment of a nerve stimulating drill bit.
Figure 6:
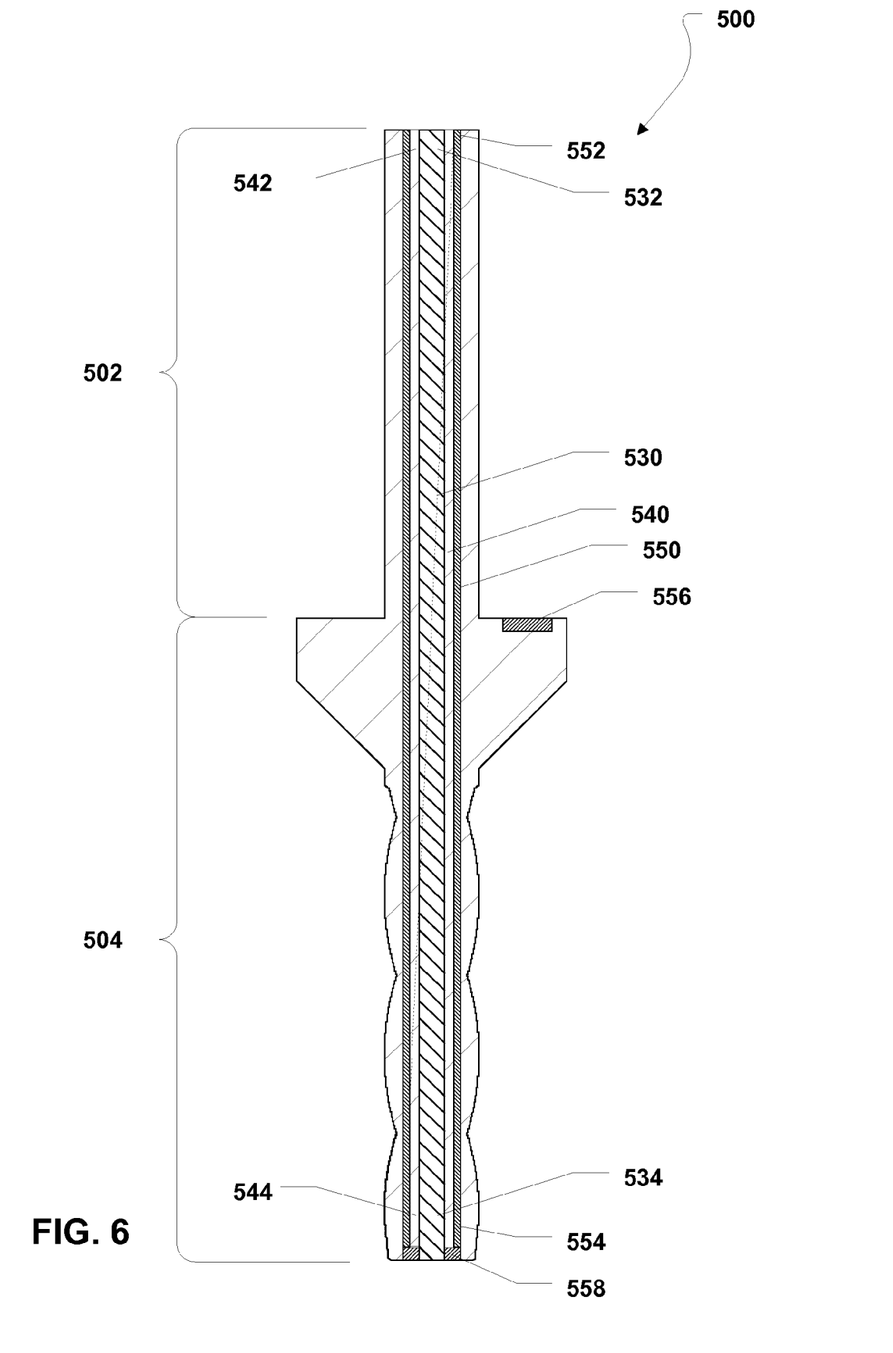
FIG. 6 is a cross-section view of the third embodiment of a nerve stimulating drill bit taken along line 6-6 in FIG. 5.

Referring to FIG. 5 and FIG. 6, a third embodiment of a nerve stimulating drill bit is shown and is generally designated 500. As shown in FIG. 5, the nerve stimulating drill bit 500 can include a shank 502 and a body 504 extending therefrom. The shank 502 can include a proximal end 506 and a distal end 508. Further, the body 504 can extend from the distal end 508 of the shank 502.

FIG. 5 illustrates that the body 504 can include a proximal end 510 and a distal end 512. Additionally, the body 504 can include a first portion 514 and a second portion 516. The first portion 514 of the body 504 can be generally frusto-conically shaped and can taper from the proximal end 510 of the body 504 toward the second portion 516 of the body 504. The second portion 516 can be generally cylindrical and can extend from the first portion 514 of the body 504 to the distal end 512 of the body 504.

As shown in FIG. 5, the second portion 516 of the body 504 can include a plurality of flutes 518 that can extend helically along the length of the second portion 516 of the body 504 from the interface with the first portion 514 of the body 504 to a cutting tip 520 at the distal end 512 of the body 504. FIG. 5 shows that the first portion 514 of the body 504 can include an angled outer perimeter 522. Moreover, a plurality of angled cutting edges 524 can extend along the angled outer perimeter 522 of the first portion 514 of the body 504.

During use, the second portion 516 of the body 504 can be used to cut a cylindrical hole in tissue, e.g., bone, and the first portion 514 of the body 504 can be used to cut an angled hole at the opening of the hole cut by the second portion 516. Accordingly, the angled portion of the hole cut using the nerve stimulating drill bit 500 can be considered a countersink portion and can allow a bone screw installed in the hole to be counter sunk in the tissue.

In a particular embodiment, the shank 502 can be generally cylindrical and can be sized and shaped to be received within a drill chuck, e.g., a keyed drill chuck, a keyless drill chuck, or any other type of drill chuck well known in the art. Alternatively, the shank 502 can be formed with a plurality of flat surfaces that will allow the drill chuck to grip the shank 502 and prevent the nerve stimulating drill bit 500 from moving within the drill chuck after the drill chuck is tightened there around.

In a particular embodiment, the shank 502 and the body 504 of the nerve stimulating drill bit 500 can be made from a dielectric material, i.e., a material that cannot conduct electricity. For example, the dielectric material can be a polymer material, a ceramic material, or a combination thereof. The polymer materials can include polyaramide materials, polyimid materials, polyamide materials, polyaryletherketone (PAEK) materials, or a combination thereof. The PAEK materials can include polyetherketone (PEK), polyetheretherketone (PEEK), polyetherketoneketone (PEKK), polyetherketoneetherketoneketone (PEKEKK), or a combination thereof. The ceramic materials can include alumina oxide, silica oxide, zirconium oxide, aluminum oxide, or a combination thereof.

Referring to FIG. 6, a cross-section of the nerve stimulating drill bit 500 is shown. As illustrated in FIG. 6, the nerve stimulating drill bit 500 can include a first conductor 530 therein. In a particular embodiment, the first conductor 530 can be generally cylindrical and can include a proximal end 532 and a distal end 534. FIG. 6 also indicates that an insulator 540 can surround the first conductor 530. The insulator 540 can be generally hollow and generally cylindrical. Further, the insulator 540 can include a proximal end 542 and a distal end 544. Moreover, a second conductor 550 can surround the insulator 540. The second conductor 550 can also define a proximal end 552 and a distal end 554.

In a particular embodiment, the conductors 530, 550 can be made from a conductive material, e.g., a metal material. The metal material can be a pure metal, a metal alloy, or a combination thereof. The pure metal can include aluminum, copper, gold, titanium, or a combination thereof. The metal alloy can include stainless steel, tungsten carbide, a cobalt-chrome-molybdenum alloy, a titanium alloy, or a combination thereof.

The insulator 540 can be made from a dielectric material, i.e. a material that cannot conduct electricity. For example, the dielectric material can be a polymer material, a ceramic material, or a combination thereof. The polymer materials can include polyaramide materials, polyimid materials, polyamide materials, polyaryletherketone (PAEK) materials, or a combination thereof. The PAEK materials can include polyetherketone (PEK), polyetheretherketone (PEEK), polyetherketoneketone (PEKK), polyetherketoneetherketoneketone (PEKEKK), or a combination thereof. The ceramic materials can include alumina oxide, silica oxide, zirconium oxide, aluminum oxide, or a combination thereof.

When the nerve stimulating drill bit 500 is installed in a surgical drill, the proximal end 532 of the conductor 530 can engage a power source that can be used to provide an electric signal to the conductor 530. Further, the second conductor 550 can engage a lead from a sensing device. The insulator 540 can insulate the conductors 530, 550 from each other. Further, the shank 502 and the body 504 of the nerve stimulating drill bit 500 can insulate the second conductor 550, e.g., from a drill chuck, a user, or patient. The nerve stimulating drill bit 500 is configured so that a signal can be transmitted into tissue via the distal end 534 of the first conductor 530. The distal end 554 of the second conductor 550 can be used to sense the signal and determine the type of tissue in which the nerve stimulating drill bit 500 is drilling. A sensing device coupled to the nerve stimulating drill bit 500 can determine the type of tissue based on the impedance of the signal transmitted and received at the nerve stimulating drill bit 500.

In an alternative embodiment, the nerve stimulating drill bit 500 can be rotated manually, e.g., by a manually operated drill or by a handle affixed directly to the nerve stimulating drill bit 500.

FIG. 6 also illustrates that the nerve stimulating drill bit 500 can include a radio frequency identification (RFID) device 556 incorporated therein. For example, the RFID device 556 can be incorporated into the body 504 of the nerve stimulating drill bit 500. Further, the RFID device 556 can be passive and can be powered by an RFID reader placed near the nerve stimulating drill bit 500. Alternatively, the RFID device 556 can be active and the nerve stimulating drill bit 500 can include a power source, such as a battery (not shown). In a particular embodiment, the RFID device 556 can identify a size of the nerve stimulating drill bit 500; a date of manufacture of the nerve stimulating drill bit 500; a lot code associated with the production of the nerve stimulating drill bit 500; a type of material, or materials, comprising the nerve stimulating drill bit 500; or a combination thereof.

As further shown in FIG. 6, the nerve stimulating drill bit 500 can include a guide device 558 incorporated into the distal end 512 of the body 504. The guide device 558 can be radiopaque and can aid in navigating the cutting tip 520 of the nerve stimulating drill bit 500 as the nerve stimulating drill bit 500 is advanced into tissue.

Description of a Fourth Embodiment of a Nerve Stimulating Drill Bit

Figure 7:
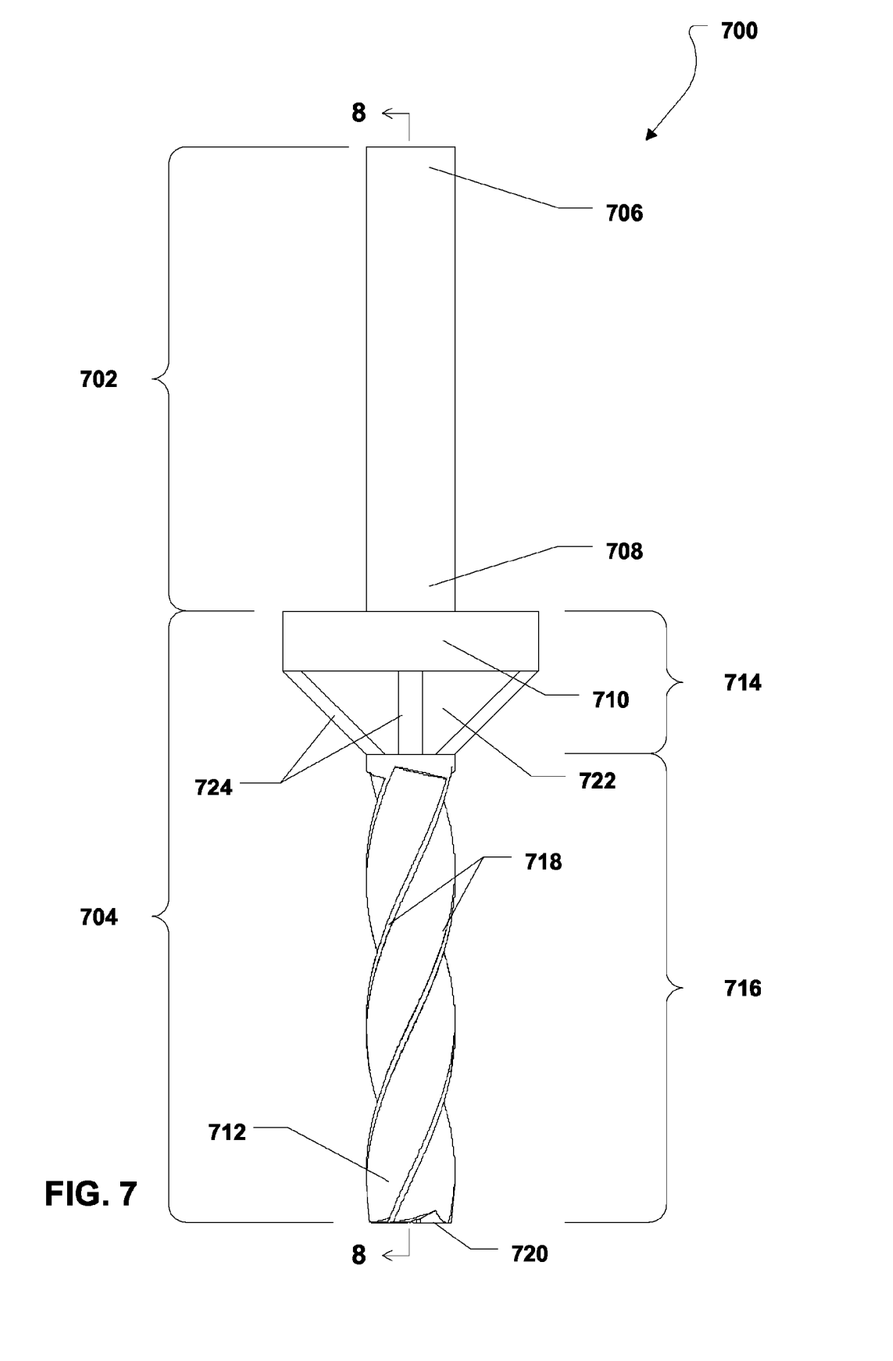
FIG. 7 is a plan view of a fourth embodiment of a nerve stimulating drill bit.
Figure 8:
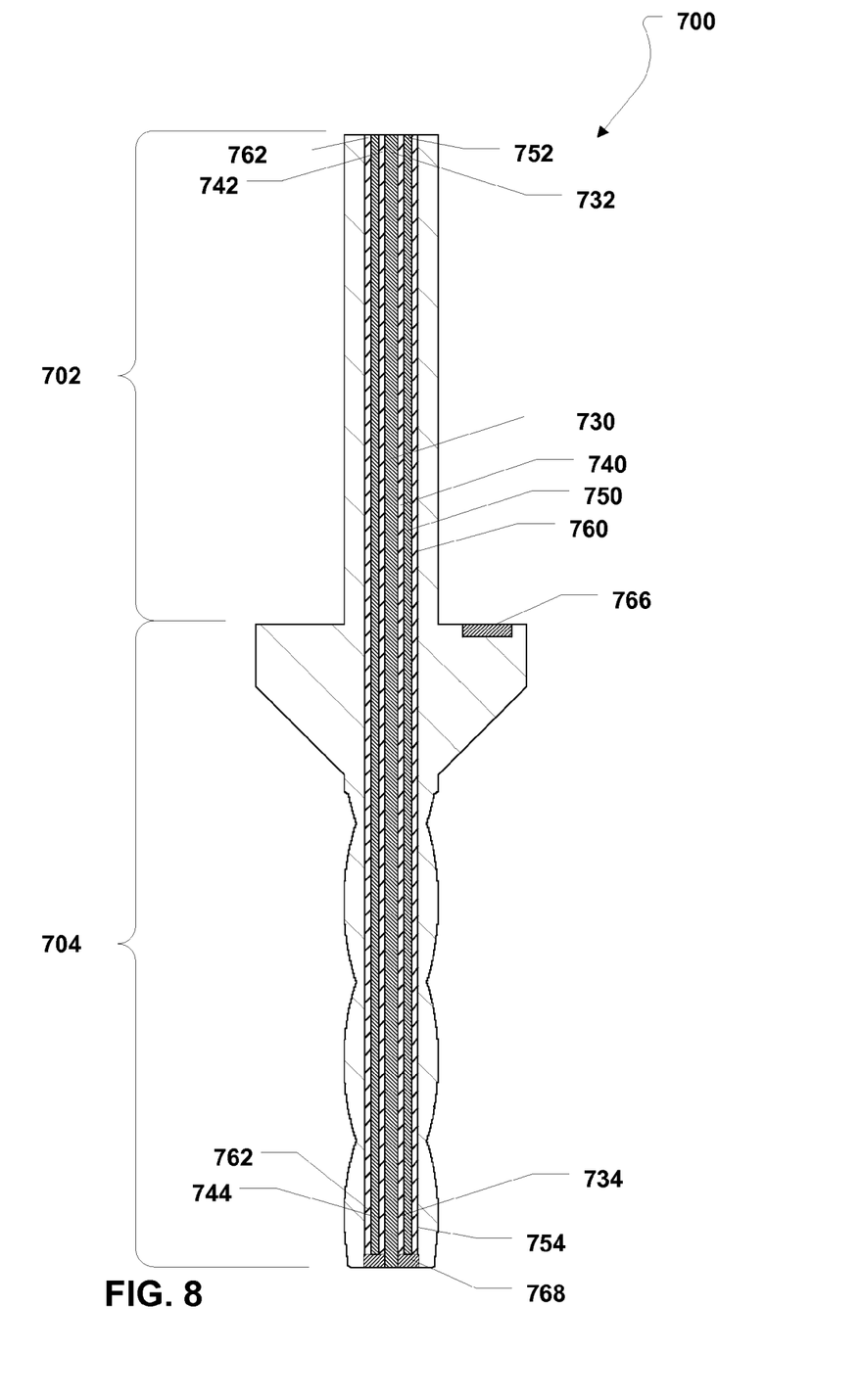
FIG. 8 is a cross-section view of the fourth embodiment of a nerve stimulating drill bit taken along line 8-8 in FIG. 7.

Referring to FIG. 7 and FIG. 8, a fourth embodiment of a nerve stimulating drill bit is shown and is generally designated 700. As shown in FIG. 7, the nerve stimulating drill bit 700 can include a shank 702 and a body 704 extending therefrom. The shank 702 can include a proximal end 706 and a distal end 708. Further, the body 704 can extend from the distal end 708 of the shank 702.

FIG. 7 illustrates that the body 704 can include a proximal end 710 and a distal end 712. Additionally, the body 704 can include a first portion 714 and a second portion 716. The first portion 714 of the body 704 can be generally frusto-conically shaped and can taper from the proximal end 710 of the body 704 toward the second portion 716 of the body 704. The second portion 716 can be generally cylindrical and can extend from the first portion 714 of the body 704 to the distal end 712 of the body 704.

As shown in FIG. 7, the second portion 716 of the body 704 can include a plurality of flutes 718 that can extend helically along the length of the second portion 716 of the body 704 from the interface with the first portion 714 of the body 704 to a cutting tip 720 at the distal end 712 of the body 704. FIG. 7 shows that the first portion 714 of the body 704 can include an angled outer perimeter 722. Moreover, a plurality of angled cutting edges 724 can extend along the angled outer perimeter 722 of the first portion 714 of the body 704.

During use, the second portion 716 of the body 704 can be used to cut a cylindrical hole in tissue, e.g., bone, and the first portion 714 of the body 704 can be used to cut an angled hole at the opening of the hole cut by the second portion 716. Accordingly, the angled portion of the hole cut using the nerve stimulating drill bit 700 can be considered a countersink portion and can allow a bone screw installed in the hole to be counter sunk in the tissue.

In a particular embodiment, the shank 702 can be generally cylindrical and can be sized and shaped to be received within a drill chuck, e.g., a keyed drill chuck, a keyless drill chuck, or any other type of drill chuck well known in the art. Alternatively, the shank 702 can be formed with a plurality of flat surfaces that will allow the drill chuck to grip the shank 702 and prevent the nerve stimulating drill bit 700 from moving within the drill chuck after the drill chuck is tightened there around.

In a particular embodiment, the shank 702 and the body 704 of the nerve stimulating drill bit 700 can be made from a metal material. The metal material can be a pure metal, a metal alloy, or a combination thereof. The pure metal can include titanium. The metal alloy can include stainless steel, tungsten carbide, a cobalt-chrome-molybdenum alloy, a titanium alloy, or a combination thereof.

Referring to FIG. 8, a cross-section of the nerve stimulating drill bit 700 is shown. As illustrated in FIG. 8, the nerve stimulating drill bit 700 can include a first conductor 730 therein. In a particular embodiment, the conductor first 730 can include a proximal end 732 and a distal end 734. FIG. 8 also indicates that an insulator 740 can surround the first conductor 730. The insulator 740 can include a proximal end 742 and a distal end 744. Moreover, a second conductor 750 can surround the insulator 740. The second conductor 750 can also define a proximal end 752 and a distal end 754. As shown in FIG. 8, a second insulator 760 can surround the second conductor 750. The second insulator 760 can include a proximal end 762 and a distal end 764.

In a particular embodiment, the conductors 730, 750 can be generally cylindrical. Further, the conductors 730, 750 can be made from a conductive material, e.g., a metal material. The metal material can be a pure metal, a metal alloy, or a combination thereof. The pure metal can include aluminum, copper, gold, titanium, or a combination thereof. The metal alloy can include stainless steel, tungsten carbide, a cobalt-chrome-molybdenum alloy, a titanium alloy, or a combination thereof.

In a particular embodiment, the insulators 740, 760 can be generally hollow and generally cylindrical. Also, the insulators 740, 760 can be made from a dielectric material, i.e., a material that cannot conduct electricity. For example, the dielectric material can be a polymer material, a ceramic material, or a combination thereof. The polymer materials can include polyaramide materials, polyimid materials, polyamide materials, polyaryletherketone (PAEK) materials, or a combination thereof. The PAEK materials can include polyetherketone (PEK), polyetheretherketone (PEEK), polyetherketoneketone (PEKK), polyetherketoneetherketoneketone (PEKEKK), or a combination thereof. The ceramic materials can include alumina oxide, silica oxide, zirconium oxide, aluminum oxide, or a combination thereof.

When the nerve stimulating drill bit 700 is installed in a surgical drill, the proximal end 732 of the first conductor 730 can engage a power source that can be used to provide an electric signal to the conductor 730. Further, the second conductor 750 can engage a lead from a sensing device. The insulators 740, 760 can insulate the conductors 730, 750 from each other and from the shank 702 and the body 704 of the nerve stimulating drill bit 700. The nerve stimulating drill bit 700 is configured so that a signal can be transmitted into tissue via the distal end 734 of the first conductor 730. The distal end 754 of the second conductor 750 can be used to sense the signal and determine the type of tissue in which the nerve stimulating drill bit 700 is drilling. A sensing device coupled to the nerve stimulating drill bit 700 can determine the type of tissue based on the impedance of the signal transmitted and received at the nerve stimulating drill bit 700.

In an alternative embodiment, the nerve stimulating drill bit 800 can be rotated manually, e.g., by a manually operated drill or by a handle affixed directly to the nerve stimulating drill bit 800.

FIG. 8 also illustrates that the nerve stimulating drill bit 700 can include a radio frequency identification (RFID) device 766 incorporated therein. For example, the RFID device 766 can be incorporated into the body 704 of the nerve stimulating drill bit 700. Further, the RFID device 766 can be passive and can be powered by an RFID reader placed near the nerve stimulating drill bit 700. Alternatively, the RFID device 766 can be active and the nerve stimulating drill bit 700 can include a power source, such as a battery (not shown). In a particular embodiment, the RFID device 766 can identify a size of the nerve stimulating drill bit 700; a date of manufacture of the nerve stimulating drill bit 700; a lot code associated with the production of the nerve stimulating drill bit 700; a type of material, or materials, comprising the nerve stimulating drill bit 700; or a combination thereof.

As further shown in FIG. 8, the nerve stimulating drill bit 700 can include a guide device 768 incorporated into the distal end 712 of the body 704. The guide device 768 can be radiopaque and can aid in navigating the cutting tip 720 of the nerve stimulating drill bit 700 as the nerve stimulating drill bit 700 is advanced into tissue.

Description of a Fifth Embodiment of a Nerve Stimulating Drill Bit

Figure 9:
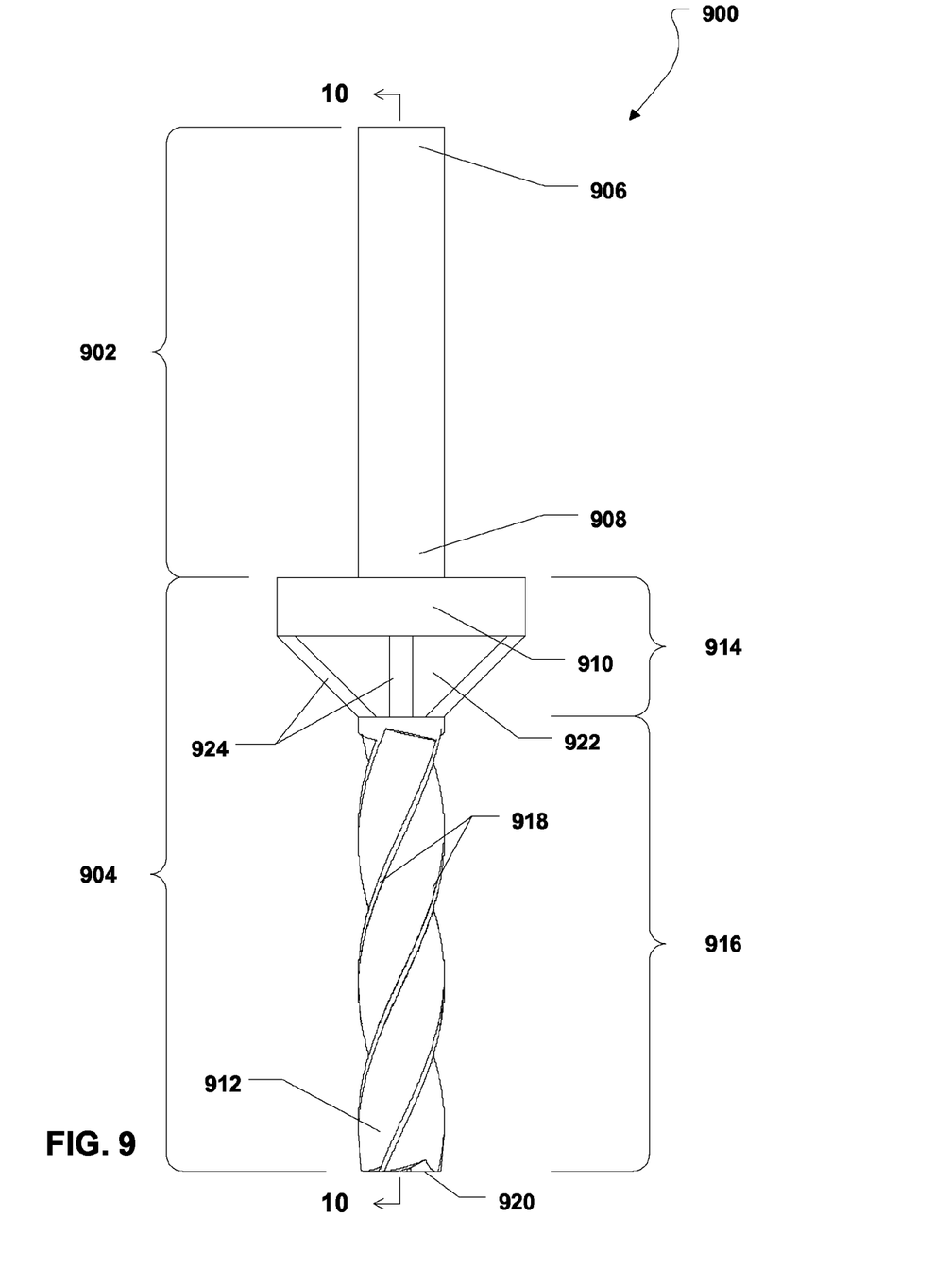
FIG. 9 is a plan view of a fourth embodiment of a nerve stimulating drill bit.
Figure 10:
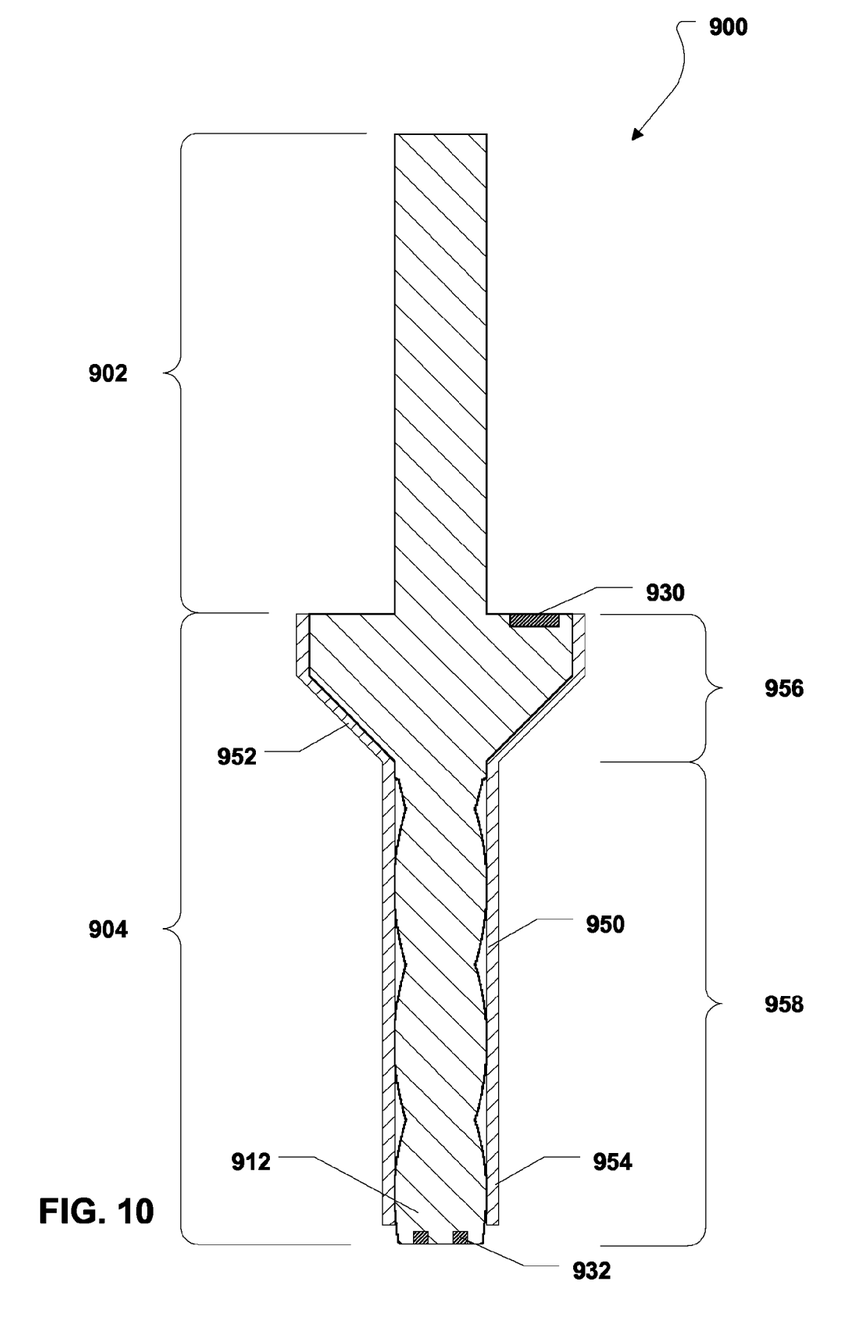
FIG. 10 is a cross-section view of the fourth embodiment of a nerve stimulating drill bit taken along line 10-10 in FIG. 9.

Referring to FIG. 9 and FIG. 10, a fifth embodiment of a nerve stimulating drill bit is shown and is generally designated 900. As shown in FIG. 9, the nerve stimulating drill bit 900 can include a shank 902 and a body 904 extending therefrom. The shank 902 can include a proximal end 906 and a distal end 908. Further, the body 904 can extend from the distal end 908 of the shank 902.

FIG. 9 illustrates that the body 904 can include a proximal end 910 and a distal end 912. Additionally, the body 904 can include a first portion 914 and a second portion 916. The first portion 914 of the body 904 can be generally frusto-conically shaped and can taper from the proximal end 910 of the body 904 toward the second portion 916 of the body 904. The second portion 916 can be generally cylindrical and can extend from the first portion 914 of the body 904 to the distal end 912 of the body 904.

As shown in FIG. 9, the second portion 916 of the body 904 can include a plurality of flutes 918 that can extend helically along the length of the second portion 916 of the body 904 from the interface with the first portion 914 of the body 904 to a cutting tip 920 at the distal end 912 of the body 904. FIG. 9 shows that the first portion 914 of the body 904 can include an angled outer perimeter 922. Moreover, a plurality of angled cutting edges 924 can extend along the angled outer perimeter 922 of the first portion 914 of the body 904.

During use, the second portion 916 of the body 904 can be used to cut a cylindrical hole in tissue, e.g., bone, and the first portion 914 of the body 904 can be used to cut an angled hole at the opening of the hole cut by the second portion 916. Accordingly, the angled portion of the hole cut using the nerve stimulating drill bit 900 can be considered a countersink portion and can allow a bone screw installed in the hole to be counter sunk in the tissue.

In a particular embodiment, the shank 902 can be generally cylindrical and can be sized and shaped to be received within a drill chuck, e.g., a keyed drill chuck, a keyless drill chuck, or any other type of drill chuck well known in the art. Alternatively, the shank 902 can be formed with a plurality of flat surfaces that will allow the drill chuck to grip the shank 902 and prevent the nerve stimulating drill bit 900 from moving within the drill chuck after the drill chuck is tightened there around.

In a particular embodiment, the shank 902 and the body 904 of the nerve stimulating drill bit 900 can be made from a conductive material, e.g., a metal material. The metal material can be a pure metal, a metal alloy, or a combination thereof. The pure metal can include aluminum, copper, gold, titanium, or a combination thereof. The metal alloy can include stainless steel, tungsten carbide, a cobalt-chrome-molybdenum alloy, a titanium alloy, or a combination thereof.

Referring to FIG. 10, a cross-section of the nerve stimulating drill bit 900 is shown. As illustrated that the nerve stimulating drill bit 900 can include a radio frequency identification (RFID) device 930 incorporated therein. For example, the RFID device 930 can be incorporated into the body 904 of the nerve stimulating drill bit 900. Further, the RFID device 930 can be passive and can be powered by an RFID reader placed near the nerve stimulating drill bit 900. Alternatively, the RFID device 930 can be active and the nerve stimulating drill bit 900 can include a power source, such as a battery (not shown). In a particular embodiment, the RFID device 930 can identify a size of the nerve stimulating drill bit 900; a date of manufacture of the nerve stimulating drill bit 900; a lot code associated with the production of the nerve stimulating drill bit 900; a type of material, or materials, comprising the nerve stimulating drill bit 900; or a combination thereof.

As further shown in FIG. 10, the nerve stimulating drill bit 900 can include a guide device 932 incorporated into the distal end 912 of the body 904. The guide device 932 can be radiopaque and can aid in navigating the cutting tip 920 of the nerve stimulating drill bit 900 as the nerve stimulating drill bit 900 is advanced into tissue.

Further, as indicated in FIG. 10, the nerve stimulating drill bit 900 can include an insulating sleeve 950 that can surround all or a portion of the body 904 of the nerve stimulating drill bit 900. The insulating sleeve 950 can include a proximal end 952 and a distal end 954. The insulating sleeve 950 can extend at least partially along the length of the body 904 of the nerve stimulating drill bit 900. For example, the insulating sleeve 950 can include a first portion 956 and a second portion 958. The first portion 956 of the insulating sleeve 950 can be generally frusto-conically shaped and can taper from the proximal end 952 of the insulating sleeve 950 toward the second portion 958 of the insulating sleeve 950. The second portion 958 can be generally cylindrical and can extend from the first portion 956 of the insulating sleeve 950 to the distal end 954 of the insulating sleeve 950. As such, the insulating sleeve 950 can be sized and shaped to fit around the body 904 of the nerve stimulating drill bit 900.

In a particular embodiment, the insulating sleeve 950 can be made from a dielectric material, i.e., a material that cannot conduct electricity. For example, the dielectric material can be a polymer material, a ceramic material, or a combination thereof. The polymer materials can include polyaramide materials, polyimid materials, polyamide materials, polyaryletherketone (PAEK) materials, or a combination thereof. The PAEK materials can include polyetherketone (PEK), polyetheretherketone (PEEK), polyetherketoneketone (PEKK), polyetherketoneetherketoneketone (PEKEKK), or a combination thereof. The ceramic materials can include alumina oxide, silica oxide, zirconium oxide, aluminum oxide, or a combination thereof.

When the nerve stimulating drill bit 900 is installed in a surgical drill, the proximal end 906 of the shank 902 can engage a power source that can be used to provide an electric signal to the nerve stimulating drill bit 900. The electric signal can have a constant current that is less than or equal to fifty milliamps (50 ma). Since the shank 902 and the body 904 of the nerve stimulating drill bit 900 are made from a conductive material, electricity can be conducted through the nerve stimulating drill bit 900. Further, the insulating sleeve 950 can be placed around the body 904 of the nerve stimulating drill bit 900 such that the distal end 912 of the body 904 extends beyond the distal end 954 of the insulating sleeve 950.

As such, the nerve stimulating drill bit 900 can be configured so the distal end 912 of the body 904 can stimulate tissue proximate to the cutting tip 920 of the nerve stimulating drill bit 900. The insulating sleeve 950 can be placed around the body 904 of the nerve stimulating drill bit 900 and the insulating sleeve 950 can substantially insulate other tissue surrounding the nerve stimulating drill bit 900 from the signal provided to the conductor 930. In a particular embodiment, a pilot hole can be drilled using another drill bit to accommodate the insulating sleeve 950. Thereafter, the insulating sleeve 950 and the nerve stimulating drill bit 900 can be placed in the pilot hole and the nerve stimulating drill bit 900 can be used to further drill into tissue while stimulating the tissue. In a particular embodiment, the insulating sleeve 950 can be removed after use of the nerve stimulating drill bit 900 or the insulating sleeve 950 can be left in place in the patient until the final bone screw is placed in the patient.

In an alternative embodiment, the nerve stimulating drill bit 900 can be rotated manually, e.g., by a manually operated drill or by a handle affixed directly to the nerve stimulating drill bit 900.

Description of a Method of Treating a Patient

Figure 11:
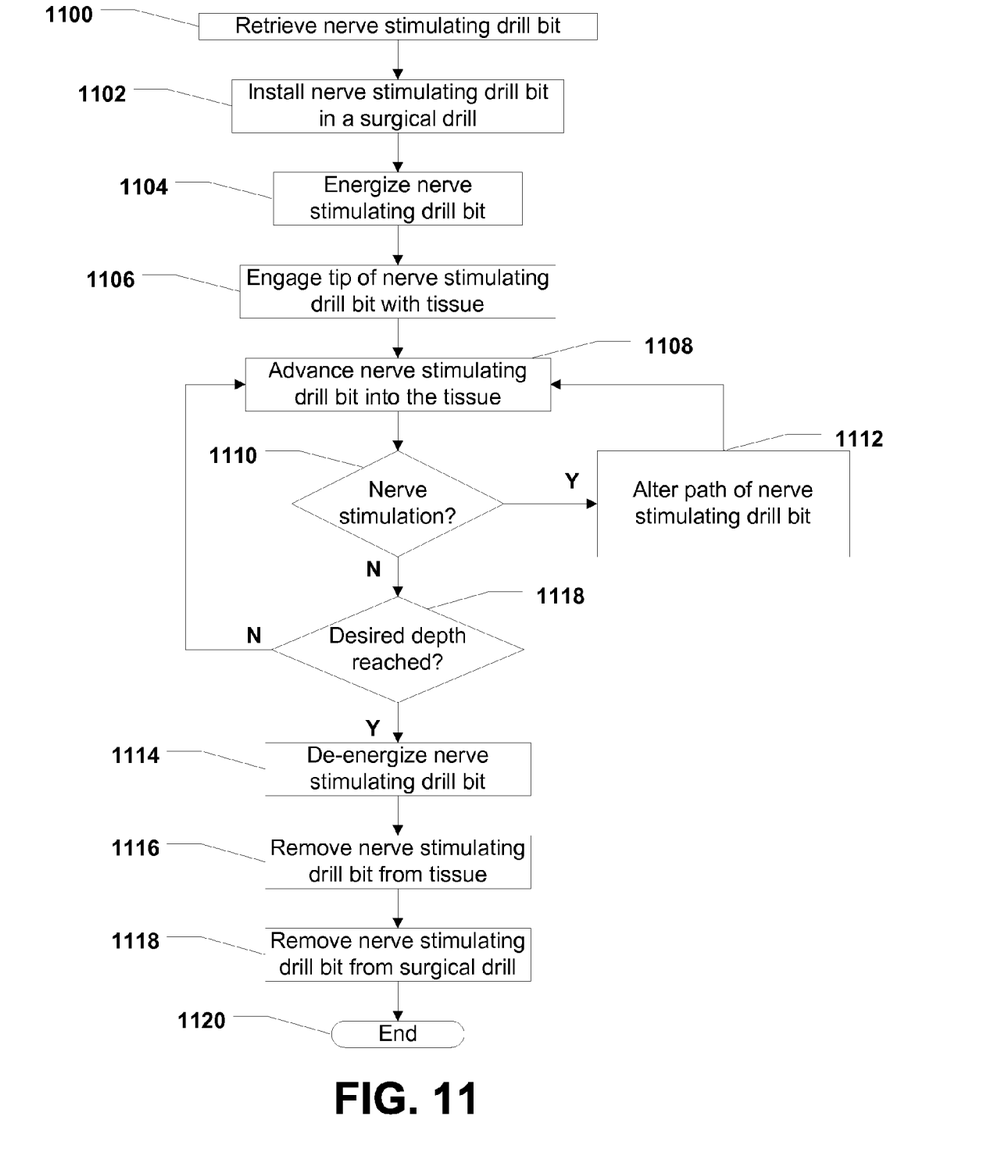
FIG. 11 is a flow chart illustrating a method of treating a patient using a nerve stimulating drill bit.

Referring now to FIG. 11, a method of treating a patient is shown and commences at block 1100. At block 1100, a nerve stimulating drill bit can be retrieved. At block 1102, the nerve stimulating drill bit can be installed within a surgical drill. The surgical drill can be configured to transmit an electrical signal to the nerve stimulating drill bit.

Moving to block 1104, the nerve stimulating drill bit can be energized. Further, at block 1106, the tip of the nerve stimulating drill bit can be engaged with tissue. At block 1108, the nerve stimulating drill can be advanced into the tissue. Proceeding to decision step 1110, it can be determined whether nerve stimulation has occurred. This determination can be made using electromyography. More specifically, this determination can be made by monitoring a location on the patient, e.g., a muscle, that corresponds to the nerve or nerves at the location being drill. When nerve stimulation occurs, the corresponding muscle or muscles contract in response to the electrical stimulation.

At decision step 1110, if nerve stimulation occurs, the method can move to block 1112, and the path of the nerve stimulating drill bit can be altered. Thereafter, the method can return to block 1108 and continue as described herein. Returning to decision step 1110, if nerve stimulation does not occur, the method can move to decision step 1118 and it can be determined whether the desired drill depth is reached. If the desired drill depth is not reached, the method can return to block 1108 and continue as described herein. On the other hand, if the desired drill depth is reached, the method can continue to block 1114 and the nerve stimulating drill bit can be de-energized. At block 1116, the nerve stimulating drill can be removed from the tissue. Thereafter, at block 1118, the nerve stimulating drill bit can be removed from the surgical drill. The method can then end at state 1120.

During use, the nerve stimulating drill bit may also be used to determine the type of tissue into which the nerve stimulating drill bit is advancing. For example, the nerve stimulating drill bit can transmit and receive a signal. The impedance of the signal can be measured and used to determine if the tip of the nerve stimulating drill bit is advancing into hard tissue, e.g., bone, soft tissue, e.g., flesh, or subcutaneous fluid.

CONCLUSION

With the configuration of structure described above, the nerve stimulating drill bit device provides a device that can be used for electromyography (EMG) and impedance measurements. For example, the nerve stimulating drill bit can provide a monopolar electric signal to tissue while the nerve stimulating drill bit is advancing into and cutting the tissue. When a nerve is stimulated, an EMG response can occur and a direction of the nerve stimulating drill can be altered to prevent damage to the nerve.

Additionally, the nerve stimulating drill bit can deliver a bipolar signal, i.e., the nerve stimulating drill bit can transmit a signal via a first conductor and receive at least a portion of the signal at a second conductor. A processor coupled to the nerve stimulating drill bit can measure the impedance of the signal and the impedance value can be used to determine if the nerve stimulating drill bit is advancing into hard tissue, soft tissue, or fluid.

The above-disclosed subject matter is to be considered illustrative, and not restrictive, and the appended claims are intended to cover all such modifications, enhancements, and other embodiments that fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A nerve stimulating drill bit, comprising:
   a shank;
   a body attached to the shank, the body having a plurality of flutes and a cutting tip; and
   a first conductor extending through the shank and the body, wherein the first conductor is insulated and provides a signal at the cutting tip, wherein the signal is configured to provide nerve stimulation at the cutting tip of the nerve stimulating drill bit.

2. The nerve stimulating drill bit of claim 1, wherein the shank and the body are contiguous and integrally formed with each other from a dielectric material.

3. The nerve stimulating drill bit of claim 2, further comprising an insulating sleeve surrounding at least a portion of the body, and wherein the dielectric material comprises at least one of a polymer material and a ceramic material.

4. The nerve stimulating drill bit of claim 3 wherein the polymer material comprises at least one of a polyaramide material, a polyimid material, a polyamide material and a polyaryletherketone (PAEK) material.

5. The nerve stimulating drill bit of claim 4, wherein the PAEK material comprises at least one of polyetherketone (PEK), polyetheretherketone (PEEK), polyetherketoneketone (PEKK) and polyetherketoneetherketoneketone (PEKEKK).

6. The nerve stimulating drill bit of claim 3, wherein the ceramic material comprises at least one of alumina oxide, silica oxide, zirconium oxide and aluminum oxide.

7. The nerve stimulating drill bit of claim 1, wherein the shank and the body comprise a metal material and are coaxial with the first conductor.

8. The nerve stimulating drill bit of claim 7, wherein the metal material comprises at least one of a pure metal and a metal alloy, or a combination thereof.

9. The nerve stimulating drill bit of claim 8, wherein the pure metal comprises titanium.

10. The nerve stimulating drill bit of claim 8, wherein the metal alloy comprises at least one of stainless steel, tungsten carbide, a cobalt-chrome-molybdenum alloy and a titanium alloy.

11. The nerve stimulating drill bit of claim 7, further comprising a first insulator around and coaxial with the first conductor.

12. The nerve stimulating drill bit of claim 11, further comprising a second conductor around and coaxial with the first insulator, wherein the nerve stimulating drill bit is configured to transmit a signal via the first conductor and receive at least a portion of the signal via the second conductor.

13. The nerve stimulating drill bit of claim 12, further comprising a second insulator around and coaxial with the second conductor.

14. The nerve stimulating drill bit of claim 1, further comprising a radio frequency identification device (RFID) within at least one of the shank and the body, and the RFID contains data about the nerve stimulating drill bit.

15. The nerve stimulating drill bit of claim 1, further comprising a guide device incorporated therein to aid in navigating the cutting tip as the nerve stimulating drill bit is advanced into tissue.

16. The nerve stimulating drill bit of claim 15, wherein the guide device is incorporated in the nerve stimulating drill bit proximal to the cutting tip.

17. The nerve stimulating drill bit of claim 16, wherein the guide device comprises a radiopaque material, and the body has a counter-sink portion with a plurality of angled cutting edges between the shank and the plurality of flutes.

18. A method of treating a patient, comprising:
energizing a nerve stimulating drill bit, wherein the nerve stimulating drill bit provides a nerve stimulation signal at a cutting tip of the nerve stimulating drill bit; and
advancing the nerve stimulating drill bit into tissue in order to cut a pilot hole in the tissue for installation of a screw.

19. The method of claim 18, further comprising:
determining whether any nerve stimulation is occurring.

20. The method of claim 19, further comprising:
altering a path of the nerve stimulating drill bit when nerve stimulation occurs.

21. The method of claim 20, further comprising:
determining whether a desired depth is reached.

22. The method of claim 21, further comprising:
de-energizing the nerve stimulating drill bit.

23. The method of claim 22, further comprising:
removing the nerve stimulating drill bit from the tissue.

24. A nerve stimulating drill bit, comprising:
a shank;
a body extending from the shank;
a first conductor extending coaxially along the shank and body; and
a second conductor extending coaxially along the shank and body, wherein the nerve stimulating drill bit is configured to transmit a signal via the first conductor and receive at least a portion of the signal via the second conductor.

25. A nerve stimulating drill bit, comprising:
a shank;
a body extending from the shank; and
a sleeve at least partially surrounding the body and at least partially extending along the body, wherein the shank and the body of the nerve stimulating drill bit comprise a conductive material and wherein the sleeve comprises a dielectric material.

* * * * *